US011207515B2

(12) United States Patent
Wax (10) Patent No.: US 11,207,515 B2
(45) Date of Patent: Dec. 28, 2021

(54) INJECTION PORT PROTECTOR (71) Applicant: Icahn School of Medicine at Mount Sinai, New York, NY (US)

(72) Inventor: David B. Wax, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 143 days.

(21) Appl. No.: 16/087,399

(22) PCT Filed: Mar. 24, 2017

(86) PCT No.: PCT/US2017/024035
§ 371 (c)(1),
(2) Date: Sep. 21, 2018

(87) PCT Pub. No.: WO2017/165779
PCT Pub. Date: Sep. 28, 2017

(65) Prior Publication Data
US 2020/0197684 A1 Jun. 25, 2020

Related U.S. Application Data (60) Provisional application No. 62/313,077, filed on Mar. 24, 2016.

(51) Int. Cl.
*A61M 39/10* (2006.01)
*A61M 5/14* (2006.01)
(Continued)

(52) U.S. Cl.
CPC ............ *A61M 39/105* (2013.01); *A61M 5/14* (2013.01); *A61M 39/20* (2013.01); *A61M 39/22* (2013.01);
(Continued)

(58) Field of Classification Search
CPC ...... A61M 39/105; A61M 5/14; A61M 39/20; A61M 39/22; A61M 39/28;
(Continued)

(56) References Cited

U.S. PATENT DOCUMENTS 3,583,460 A 6/1971 Faust et al.
4,810,241 A * 3/1989 Rogers ................. A61M 39/16
604/28

(Continued)

FOREIGN PATENT DOCUMENTS

CN 204428594 7/2015

*Primary Examiner* — Amber R Stiles
(74) *Attorney, Agent, or Firm* — Leason Ellis LLP (57) ABSTRACT A device is provided for shielding a fluid access port structure that is located along tubing that is part of an intravenous (IV) medication delivery system and is configured to permit injection of a fluid into the tubing. The device includes a body having a hollow interior and a first opening formed therein for receiving the fluid access port structure such that a side wall of the body surrounds and extends above the fluid access port structure. The body also includes a second opening through which a fluid delivery member can be inserted to allow mating between the fluid delivery member and the fluid access port structure for delivering the fluid into the tubing.

27 Claims, 5 Drawing Sheets (51) Int. Cl.
*A61M 39/20* (2006.01)
*A61M 39/22* (2006.01)
A61M 39/28 (2006.01)
A61M 39/02 (2006.01)

(52) U.S. Cl.
CPC ..... *A61M 39/28* (2013.01); *A61M 2039/0205* (2013.01); *A61M 2039/1066* (2013.01); *A61M 2039/229* (2013.01)

(58) Field of Classification Search
CPC .. A61M 2039/0205; A61M 2039/1066; A61M 2039/229; A61M 39/10; A61M 39/165
See application file for complete search history.

(56) References Cited

U.S. PATENT DOCUMENTS

| | | | |
|---|---|---|---|
| 4,878,897 A | | 11/1989 | Katzin |
| 4,946,445 A | | 8/1990 | Lynn |
| 4,963,132 A | * | 10/1990 | Gibson ................ A61M 39/20 285/331 |
| 5,061,248 A | | 10/1991 | Sacco |
| 5,069,666 A | | 12/1991 | Gericke |
| 5,084,032 A | | 1/1992 | Kornberg et al. |
| 5,423,775 A | | 6/1995 | Cannon |
| 5,964,785 A | | 10/1999 | Desecki et al. |
| 8,585,655 B2 | | 11/2013 | Bierman |
| 2007/0083166 A1 | | 4/2007 | Botich et al. |
| 2009/0182309 A1 | * | 7/2009 | Muffly ................ A61M 39/165 604/535 |
| 2010/0307510 A1 | | 12/2010 | Sabin |
| 2017/0065808 A1 | * | 3/2017 | Filz .................... A61M 39/165 |

\* cited by examiner

INJECTION PORT PROTECTOR

CROSS-REFERENCE TO RELATED PATENT APPLICATIONS

This application is a U.S. National Phase Application under 35 U.S.C. § 371 of International Patent Application No. PCT/US2017/024035, filed Mar. 24, 2017, which claims the priority of U.S. Provisional Patent Application 62/313,077, filed Mar. 24, 2016, each of which is incorporated by reference as if expressly set forth in their respective entirety herein.

TECHNICAL FIELD

The present invention generally relates to the field of medical devices and more specifically, to devices (protectors) that shield injection ports that are associated with intravenous medication delivery.

BACKGROUND

Preventing healthcare associated infections has become a major clinical and economic issue for hospitals and other similar settings. Prior studies have linked microbial contamination of intravenous (IV) ports and stopcocks (from practitioner, patient, and environmental reservoirs) with postoperative infections. It is hypothesized that these microbial contaminants gain entry to the IV tubing, IV catheter, and eventually bloodstream and cause local or distant infection.

Intravenous (IV) injection or infusion of medication means that the medication is sent directly into a person's vein (arm or hand) using a needle or tube. With IV administration, a thin plastic tube called an IV catheter is inserted into the patient's vein. The catheter allows the healthcare provider to give the patient multiple safe doses of medication without needing to poke the patient with a needle each time. IV medication is often used because of the control it provides over a dosage. For instance, in some situations, people must receive medication very quickly. This includes emergencies, such as a heart attack, stroke, or poisoning. In these instances, taking pills or liquids by mouth may not be fast enough to get these drugs into the bloodstream of the patient. IV administration, on the other hand, quickly sends the medication directly into the bloodstream so that the medication can begin working. Other times, medications may need to be given slowly but constantly. IV administration can also be a controlled way to give drugs over time to the patient. Certain drugs can be given by IV administration because if the patient took the medication orally (by mouth), enzymes in the patient' stomach or liver would break them down. This would prevent the drugs from working well when they're finally sent to the patient's bloodstream. Therefore, these drugs are much more effective if sent directly into the patient's bloodstream by IV administration.

Flow paths for gravity feeding IV solutions or infusion pump based IV solutions to a patient are generally equipped with an injection port through which medication (or other fluid) can be delivered directly into the flow line for rapid administration. The injection port typically includes a short piece of tubing that enters the main flow line at an angle and is capped at its distal end by a needle penetratable membrane. Modern needleless injection ports include a port that has a retractable rubber stopper/septum that gets pushed out of the way when a syringe is attached and then springs back and seals the port when the syringe is removed.

Medication can also be delivered into a flow line by use of a stopcock that assists the caretaker in controlling fluid flow through IV delivery systems. As is generally known, a stopcock is an externally operated valve regulating the flow of a liquid or gas through a pipe. Stopcocks that are configured for use with IV delivery systems include at least one injection port that can mate with a fluid delivery device, such as a syringe.

In both types of injection ports, there is a risk that contaminants can access the bloodstream through the injection port. One type of contamination is contact contamination in which the injection port contacts contaminated matter, such as skin of a caretaker or patient, bodily fluids, bedsheets, furniture, a floor surface, etc. In such instances, bacteria are transferred from the contaminated surface onto the injection port. It is also possible or less common that the contamination can arise from airborne contaminants.

Various techniques and devices have been shown to decrease contamination, but these are not universally practiced/used or practical. Hand washing helps decrease practitioner contamination, spread of pathogenic microbes to patients and devices (including IV ports and stopcocks) they touch, and ultimately nosocomial infections. However, compliance with frequent handwashing recommendations is often suboptimal due to inconvenience and intolerance. IV stopcocks are typically packaged with protective caps but these are often removed and then never replaced (due to inconvenience of repeated capping and uncapping), leaving the stopcock open to contamination of the fluid path. Alcohol wipes, scrubbing devices, and antimicrobial caps are available to intermittently disinfect injection ports, but they are not consistently utilized because of the time and effort they require. They are particularly inconvenient in the operating room and intensive care settings where frequent and/or rapid medication administration is necessary.

The present invention overcomes the shortcomings of existing technologies and provides barrier devices (protectors) that are configured to prevent IV tubing port and stopcock contamination.

SUMMARY

In accordance with the present invention, barrier devices (protectors) are disclosed that are configured to prevent IV tubing port and stopcock contamination.

In one embodiment, a device is provided for shielding an injection port that is located along tubing that is part of an intravenous (IV) medication delivery system. The device includes a body having a hollow interior and a first opening for receiving a fluid delivery member to allow passage of the fluid delivery member into the hollow interior while the body at least partially encapsulates the injection port. The body further includes a first slot that opens into the first opening and terminates at a closed end and a second slot spaced from the first slot. The second slot also opens into the first opening and terminates at a closed end. The body also includes first and second supports that are formed within the hollow interior and extend transversely thereacross and are formed such that at least a portion of the first slot including the closed end is located therebetween. The first and second supports are configured and positioned for receiving and holding the injection port therebetween, while the first and second slots are configured to allow coupling between the injection port and efferent and afferent limbs of the tubing.

In another embodiment, a device is provided for shielding a stopcock or injection port that is located along tubing that is part of an intravenous (IV) medication delivery system.

The device includes a body having a hollow interior and a first opening for receiving a fluid delivery member to allow passage of the fluid delivery member into the hollow interior. The body further includes a second opening that is located opposite the first opening. A connector is disposed within the second opening such that a first connector part at a first end thereof is disposed within the hollow interior and a second connector part c a second end thereof is disposed external to the body. The first connector part is at least partially encapsulated within the body thereby preventing inadvertent contact with the first connector part.

The first connector part is configured to mate with fluid delivery member and the second connector part is configured to mate with a connector associated with the stopcock or injection portarm for establishing a fluid connection between the fluid delivery member and the tubing through the stopcock.

DETAILED DESCRIPTION OF CERTAIN EMBODIMENTS

Figure 1:
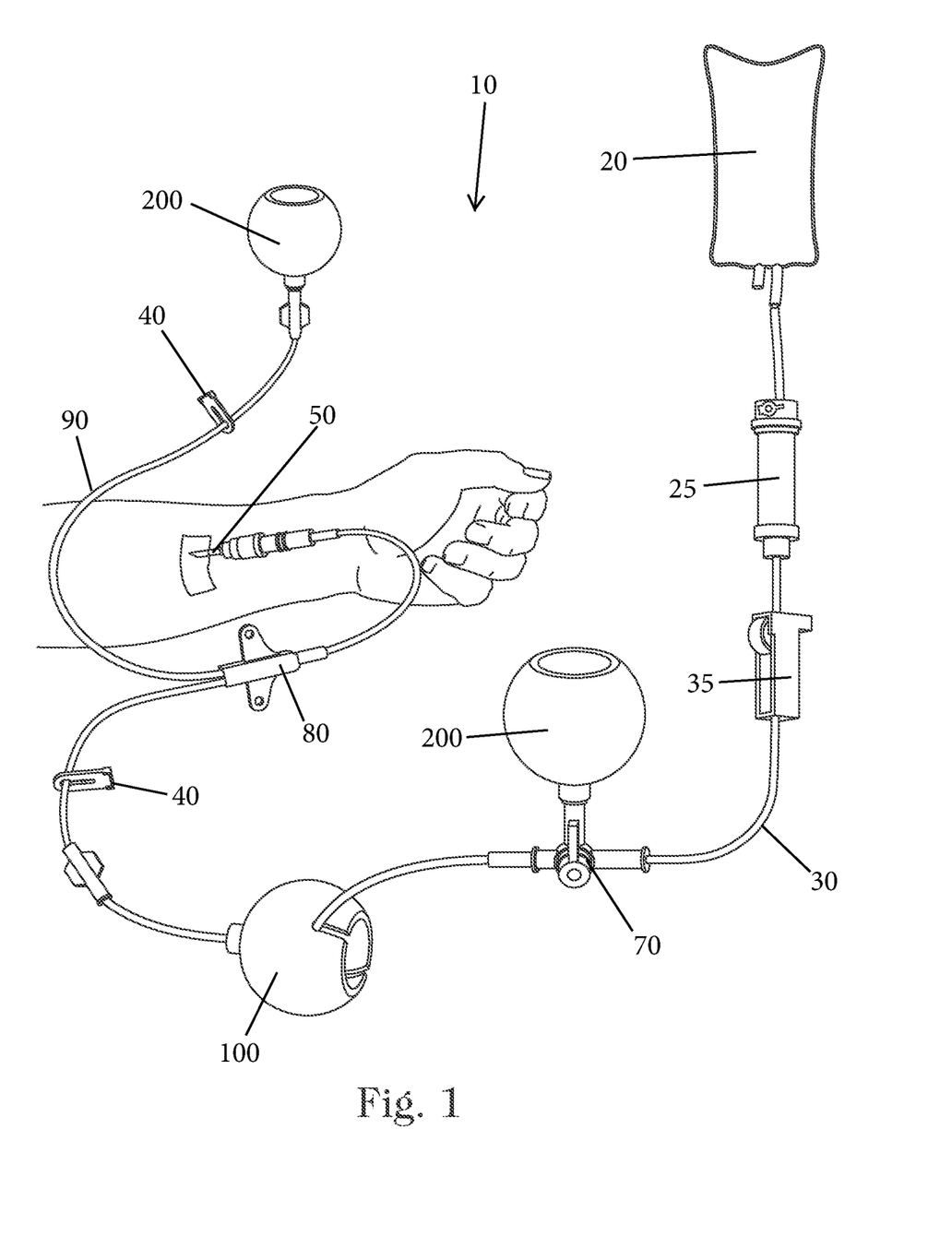
FIG. 1 is a schematic of an exemplary intravenous (IV) medication delivery system having at least one inline injection port and at least one stopcock.
Figure 2:
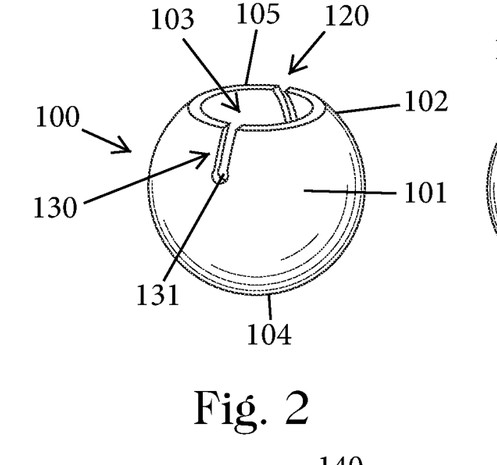
FIG. 2 is a side perspective view of a device according to a first embodiment for shielding an inline injection port to prevent surface contamination thereof.
Figure 3:
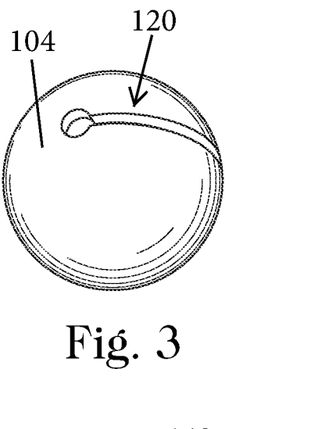
FIG. 3 is a side and bottom perspective view of the device of FIG. 2.
Figure 4:
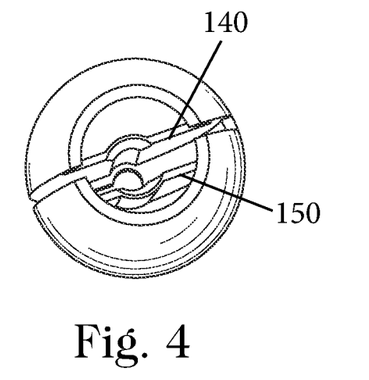
FIG. 4 is a top and side perspective view of the device of FIG. 2.
Figure 5:
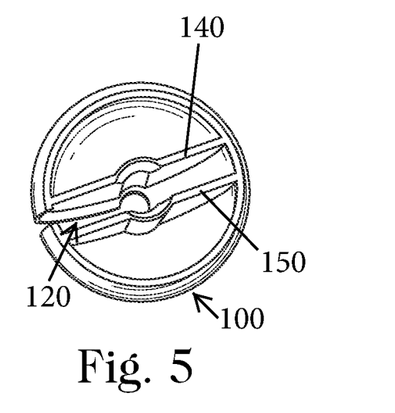
FIG. 5 is a transverse cross-sectional view of the device of FIG. 2.

FIG. 1 shows a general schematic of an exemplary intravenous (IV) medication delivery system 10. The system 10 includes a fluid source 20 (e.g., an IV fluid which is typically mostly formed of water) and typically, the fluid source 20 is in the form of an IV bag. A drip chamber 25 is located just below the IV bag 20. Inside, the drip chamber 25, one can see the fluid drip down from the IV bag 20 into IV tubing 30 (IV conduit in the form of flexible clear plastic tubing). Along the IV tubing 30 includes a roller clamp 35 which is a device that is used to control the rate at which the IV fluid infuses. If the roller clamp 35 is rolled in one direction, the roller clamp 35 squeezes the IV tubing 30 more tightly, making it narrower and therefore making the fluid flow through the IV tubing 30 more slowly. Conversely, if the roller clamp 35 is rolled in the opposite direction, the device 35 loosens its pinching of the IV tubing 30, making the IV tubing 30 less narrow, and allowing the IV fluid to flow through at a faster rate.

A slide clamp 40 is disposed along the IV tubing 30 and is configured to completely stop the IV from flowing without having to adjust the roller clamp 35. The slide clamp 40 operates by pinching the IV tubing 30 completely shut when the IV tubing 30 is slid into the narrowest part of the slide clamp 40.

A cannula 50 is a hollow needle, or more often a length of flexible plastic tubing which has been inserted into the vein (arm or hand) using a needle. The IV tubing 30 is typically taped to the patient's arm to prevent the cannula 50 from coming out when the patient moves. There are two different kinds of veins that can be used for the placement of the cannula; namely, a peripheral vein, which is any vein that is not in the torso, or a larger more central vein in the chest. Thus, a peripheral line is an IV that is attached to a peripheral vein (typically inserted to the arm of hand), while a central line is an IV that is attached to a vein in the chest.

As discussed herein, medicine or fluids other than those in the IV bag 20 are injected into the IV tubing 30 at one or more locations using one or more different techniques. For example, an inline injection port, generally shown at 60 in FIG. 1, is one type of device through which medication (or other fluid) can be delivered directly into the IV tubing 30 for rapid administration. Alternatively, and as shown also in FIG. 1, medication can also be delivered into the IV tubing 30 by use of a stopcock 70 that assists the caretaker in controlling fluid flow through IV delivery system 10. Each of the injection port 60 and stopcock 70 is described in more detail below. It will also be understood that the system 10 can be configured to deliver one more medications to the patient and thus, the system 10 can include one or more injection ports 60 and/or one or more stopcocks 70.

Moreover, the IV delivery system 10 can also include one or more other injection points at which fluid, such as medication, can be injected. For example, FIG. 1 shows a secondary line 90 that is in fluid communication with the IV tubing 30 (which represents the main IV line) and a proximal end of the secondary line 90 terminates in a secondary injection port 91 that is configured to mate with a fluid delivery member, such as a syringe, for injecting fluid into the secondary line 90 and then into the IV tubing 30 for delivery to the patient. The main line (IV tube 30) and secondary line 90 can join one another at a catheter device 80 or the like that allows the combined fluid to flow to the patient.

In accordance with the present invention, each access point at which fluid (e.g., medication) is injected into the IV tubing 30 is protected against contamination (e.g., surface and/or airborne) by a device that can be thought of as a protector. As set forth below, depending on the type of access point (e.g., injection port or stopcock type injection port), the construction of the device (protector) will vary.

Figure 6:
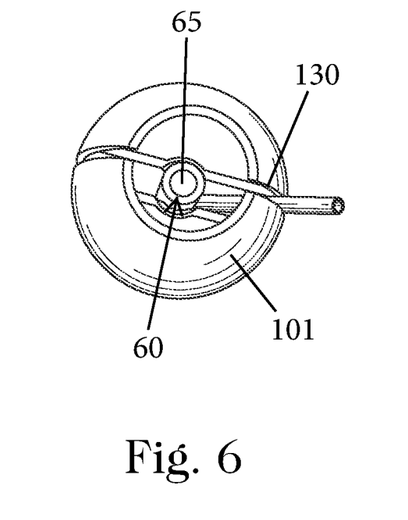
FIG. 6 is a top and side perspective view of the device of FIG. 2 with the inline injection port inserted and held therein.
Figure 7:
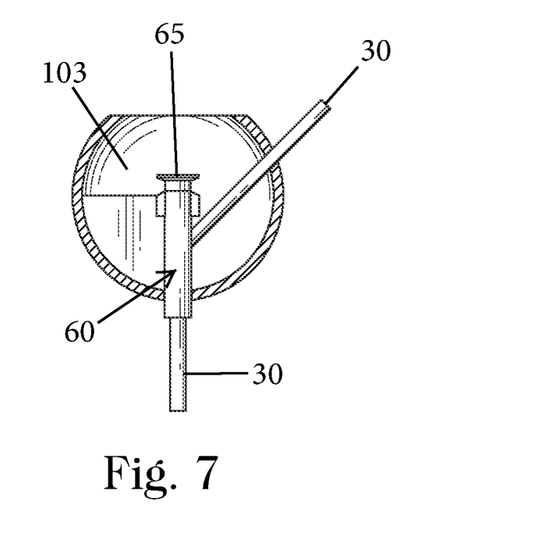
FIG. 7 is a longitudinal cross-sectional view of the device of FIG. 2 with the inline injection port inserted and held therein.
Figure 8:
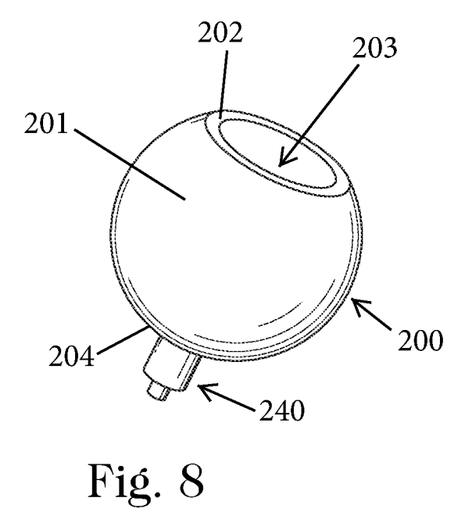
FIG. 8 is a side perspective view of a device according to a second embodiment for mating with a stopcock or injection port and providing a shielded interface through which fluid can be injected.
Figure 9:
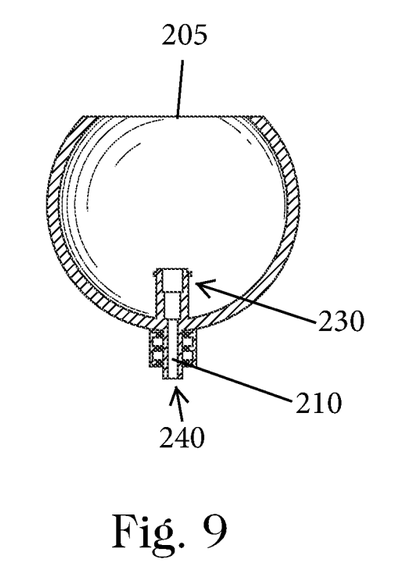
FIG. 9 is a longitudinal cross-sectional view of the device of FIG. 8.
Figure 10:
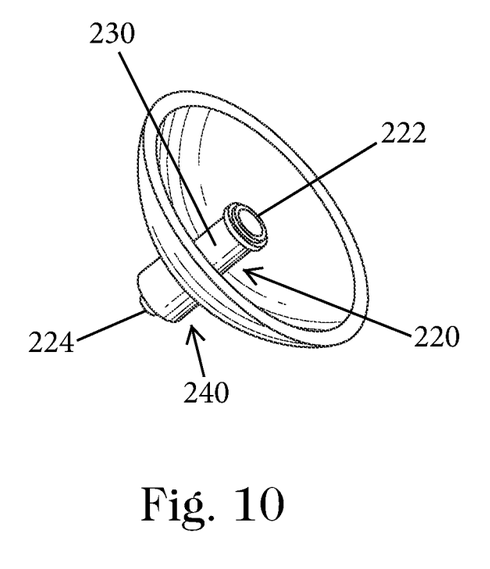
FIG. 10 is a transverse cross-sectional view of the device of FIG. 8.

FIGS. 1-7 illustrate a first device (first protector) 100 according to a first embodiment and configured to shield an injection port that is associated with intravenous medication delivery as a means for preventing contamination of the injection port. More specifically, the first device 100 is configured to mate and be used with one inline injection port 60. As shown in FIGS. 1, 6 and 7, the injection port 60 can be in the form of a Y-shaped connector that is mounted at a desired location of the flow line (IV tubing 30) close enough to the lower or infusion end of the line to enable the fluid injection through the port 60 to be rapidly administered. The injection port 60 includes a main conduit section 62 that attaches to the IV tubing 30 and an upwardly raised arm 64 that extends radially outward from the main conduit section 62 a sufficient distance to provide ready access to a needle. The distal end of the arm 64 is capped with a needless injection port septum or a needle penetratable membrane 65 which can be formed of rubber or any other suitable material that is known and used in the art. Fluid, such as medication, is thus injected through the arm 64 into the main conduit section 62 where it joins the fluid from the IV bag and is delivered through the IV tubing 30 to the patient.

As mentioned herein, the illustrated device 100 is configured to be detachably coupled to the injection port 60. The device 100 is generally in the form of a structure that surrounds the injection port 60 and more specifically, surrounds the port septum 65 so as to prevent a foreign article, such as the caretaker's hand or fingers or any other material, from contacting the port septum 65. As discussed herein. The illustrated device 100 has a wall structure that extends above the port septum 65 so as to prevent easy access to the port septum 65 and has only limited access to the center of the device 100 in which the port septum 65 is located.

The device 100 can be in the form of a hollow structure that has a hollow interior 103 in which the port septum 65 is disposed with a wall of the device 100 surrounding and shielding the port septum 65 from contact with foreign matter. The device 100 also is configured to accommodate the injection port 60 in that the device 100 allows the main conduit section 62 and the arm 64 to pass therethrough. The device 100 can thus be detachably coupled to the injection port 60.

In the illustrated embodiment, the device 100 has a generally spherical shaped body 101 with one end 102 being truncated and defining a main entrance into the hollow interior 103. It will be understood that the body 101 can have other shapes, such as a dodecahedron or other non-spherical shape so long as it has a hollow interior 103. Due to the spherical shape of the device 100, the truncation at the one end 102 defines a circular shaped opening (orifice) 105 that provides direct access to the hollow interior 103 and in particular, is sized so as to allow insertion of a syringe. An opposite end 104 of the body 101 also provides access to the hollow interior 103 in that a hole 110 is formed through the body 101. The hole 110 is formed at one end (a closed end) of a first slot 120 that is formed in the body 101. The first slot 120 extends from the hole 110 to the opening 105. As shown, the dimensions of the hole 110 can be enlarged relative to a width of the first slot 120. The hole 110 can be circular shaped and the first slot 120 can be a continuous slot having a uniform width. The first slot 120 receives the efferent limb of the IV tubing 30 and/or a portion of the inline injection port 60 that connects to the efferent limb.

The body 101 also includes a second slot 130 for receiving the afferent limb of the IV tubing 30 and/or a portion of the inline injection port 60 that connects to the afferent limb. The second slot 130 is formed in the body 101 at a location that is generally opposite the first slot 120; however, it will be appreciated that it can be formed at other locations as well to accommodate different types of injection ports 60. The second slot 130 is defined by a circular shaped hole 131 at a closed end of the second slot 130 and extends to the opening 105. Thus, each of the first and second slots 120, 130 can be accessed at the opening 105 and this permits, as described herein for insertion of the injection port 60 and the IV tubing 30. As shown, the sizes of the hole 110 and the hole 131 can be different or in some embodiments, the sizes can be the same. The first slot 120 has a longer length compared to the second slot 130.

Internally within the hollow interior 103 of the body 101 is a retaining structure that assists in holding the injection port 60 in place. For example, the retaining structure can be in the form of first and second supports (rails or brackets) 140, 150 that extend transversely across the body 101 and more particularly, extends transversely along a bottom surface of the body 101. Since the body 101 has a spherical shape, the bottom surface has a concave shape. The first and second supports 140, 150 can be in the form of upstanding rails that protrude upwardly from the bottom surface. The first and second supports 140, 150 are spaced apart from one another and portions of the first and second supports 140, 150 are located on opposite sides of the first slot 120. This placement thus locates the first slot 120 centrally between the first and second supports 140, 150.

Since the hole 110 is preferably located at the center of spherical body 101, the center portions of the first and second supports 140, 150 can be formed to accommodate the hole 110 which has an enlarged shape relative to the first slot 120 as mentioned herein. Thus, the inner surfaces of the first and second supports 140, 150 can have opposing arcuate shaped recessed portions 141, 151, respectively, so as to accommodate the injection port 60 that is received through the hole 110. The end portions of the first and second supports 140, 150 can be parallel to one another. Preferably, the heights of the first and second supports 140, 150 are the same. The first and second supports 140, 150 can be integrally formed with the body 101 as by a common molding process when the device 100 is formed of a moldable material. In FIG. 6, the first and second supports 140, 150 have been removed to allow for clearer illustration of the other components and the injection port 60.

It will be understood that the injection port 60 can comprise a rigid plastic piece that is integral to the IV tubing which can have a more flexible material characteristic relative to the rigid plastic piece. It will therefore be understood that in one embodiment, the flexible IV tubing that is attached to the rigid plastic piece (injection port 60) can be the structures that pass through the slots 120, 130, while the rigid plastic piece can be contained within the body 101. Alternatively, a portion of the rigid plastic piece may pass through the slot 120. In any event, the slots 120, 130, permit routing of the IV tubing 30 in an inline injection port scheme. The body 101 is then disposed over the injection port 60 so as to surround the injection port 60.

The use of the device 100 with the injection port (an aseptic inline injection port) 60 will be understood with reference to FIGS. 6 and 7. The injection port 60 is disposed within the hollow interior 103 by inserting the efferent limb of tubing (IV tubing 30) through the first slot 120 and by pulling the injection port 60 down through the opening 105. The injection port 60 is disposed between the first and second supports 140, 150 so that the injection port 60 becomes wedged therebetween. The afferent limb of the IV tubing 30 is inserted through the second slot 130 to hold it in place during use. The injection port 60 is held in place by the first and second supports 140, 150, preventing twisting or dislodgement during use, and is shielded from contact with contaminated surfaces by the body (shell) 101. It will be understood that the construction of the body 101 is such that the side wall of the body 101 extends above the port septum 65 so as to prevent lateral contact with the port septum 65. In the case of sphere shaped body 101, the side wall not only extends above the port septum 65 but it also has inward curvature and therefore, the side wall extends inwardly toward the port septum 65 so as to provide additional protective coverage of the port septum 65.

The body (shell) 101 thus at least partially encapsulates the port septum 65 of the injection port 60. Due to the spherical shape of the shell 101 and the location of the injection port 60 within the hollow interior 103 provides for the partial encapsulation of the injection port 60 and therefore, it is very difficult for a contaminated surface to come into contact with the port septum 65 since the only point of access to the port septum 65 is through the small opening 105 that is located above the port septum 65.

To use the injection port 60, the body (shell) 101 is grasped in the hand and a syringe is inserted through the opening 105 and medication is injected into the injection port 60 through the port septum 65. Grasping the body 101 positions the hand a distance from the injection port and thus, in the case that there is surface contamination on the hand, the contamination is prevented from contacting the port septum 65.

In yet another embodiment, the device 100 can be an integral part of the injection port 60 in that the device 100 is permanently coupled to the injection port 60 and is not meant to be separated therefrom. In other words, the shell is permanently connected to the injection port structure such that it forms a single part that is used with an IV line. In this embodiment as in the others, the device 100 at least partially encapsulates the port interface of the injection port that receives the fluid. Any number of suitable manufacturing techniques can be used to form such a structure, including bonding and molding techniques.

The device 100 can be formed of any number of different materials that are suitable for the intended application described herein. For example, the device 100 can be formed of any number of different plastic materials that can have different degrees of flexibility (e.g., rigid, semi-rigid, etc.). The device 100 is of sufficient rigidity such that when the user grasps the body 101, the body 101 maintains its shape and does not collapse so as to cause the side wall of the body 101 to make contact with the port septum 65.

Now turning to FIGS. 1 and 8-10 which depict a second device (second protector) 200 in accordance with a second embodiment of the present and intended for use with the stopcock 70. There are many different types of stopcocks 70; however, all are configured such that a pivotable lever 71 controls flow of fluid through the stopcock 70 which is in fluid communication with the IV tubing 30. In the illustrated embodiment, the stopcock 70 has main legs 72, 72 to which the IV tubing 30 is inserted so as to place the stopcock 70 in the fluid circuit. A side leg 75 is the portion of the stopcock 70 through which the medication is delivered. The pivotable lever 71 is manipulated so as to control delivery of fluid from the side leg 75 into the IV tubing 30. The side leg 75 is typically in the form of a luer connector to allow for easy connection to a syringe or the like. In the illustrated embodiment, the side leg 75 comprises a female luer connector.

The second device 200 can be in the form of a hollow structure that has a hollow interior 203 into which a syringe or the like can be inserted for delivering the medication to the side leg (e.g., female luer connector) 75 of the stopcock 70 in a manner in which the attachment point between the fluid delivery member (e.g., a syringe) and the second device 200 is shielded. The device 200 is configured to be detachably coupled to the stopcock 70.

In the illustrated embodiment, the second device 200 has a generally spherical shaped body 201 with one end 202 being truncated and defining a main entrance into the hollow interior 203. It will be understood that the body 201 can have other shapes, such as a dodecahedron or other non-spherical shape so long as it has a hollow interior 203. Due to the spherical shape of the device 200, the truncation at the one end 202 defines a circular shaped opening (orifice) 205 that provides direct access to the hollow interior 203 and in particular, is sized so as to allow insertion of a syringe. An opposite end 204 of the body 201 also provides access to the hollow interior 203 in that a hole or channel 210 is formed through which fluid exits the body 201.

The body 201 includes a connector 220 that is configured to mate with both the stopcock 70 and the fluid delivery member (syringe). The connector 220 is located at the bottom of the body 201 and is securely coupled (attached) to the body 201 using any number of suitable techniques including a sealed snap-fit arrangement, use of a bonding agent, a molding process in which the connector 220 is integral to the body 201, etc. The connector 220 can be integrally formed with the body 201 and has a first end 222 that has a first connector part 230 and at an opposite second end 224, a second connector part 240 is formed. The first connector part 230 is disposed within the hollow interior 203 and is thus configured to mate with the fluid delivery member, while the second connector part 240 is disposed outside of the body (shell) 201 and is thus configured to mate with the side leg 75 of the stopcock 70. For example, the first connector part 230 can be in the form of a female luer connector that is configured to mate with a distal end (e.g., a male luer connector) of the fluid delivery member. The second connector part 240 can be in the form of a male luer connector that is configured to mate with a female luer connector (side leg 75) of the stopcock 70, thereby providing a fluid connection between the fluid delivery member (syringe) and the stopcock 70 to allow controlled delivery of medication or the like into the IV tubing 30.

It will also be appreciated that there are other types of luer connectors and the connector 220 can thus be substituted with any of these types of luer connectors.

Similar to the first device 100, the second device 200 is configured such that the fluid entry point, in this case, the first connector part 230 is shielded by the body 201 from contamination, such as surface contamination. It will be understood that the construction of the body 201 is such that the side wall of the body 201 extends above the first connector part 230 so as to prevent lateral contact with the first connector part 230. In the case of sphere shaped body 201, the side wall not only extends above the first connector part 230 but it also has inward curvature and therefore, the side wall extends inwardly toward the first connector part 230 so as to provide additional protective coverage of the first connector part 230.

To use the second device 200, the body 201 is grasped in the hand and a syringe is inserted through the opening 205 and is connected to the first connector part 230 (female luer connector). The stopcock 70 is then opened, as by manipulating the lever, to permit inflow from the syringe and the medication is injected into the stopcock 70 (i.e., the side leg 75 thereof).

In yet another embodiment, the second device 200 is configured to mate to a needless luer-lock injection port that includes a needless septum. This type of injection port includes a luer type connector at one end which is configured to mate to the second connector part 240 of the device 200. Thus, device 200 is not limited to use of stopcock constructions but can be used with any luer type needleless injection port.

Figure 15:
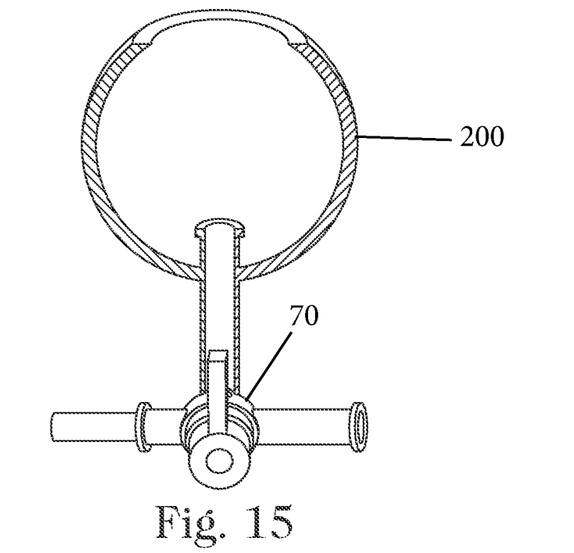
FIG. 15 is cross-sectional view showing a stopcock within integral protector.

In yet another embodiment shown in FIG. 15, the device 200 can be an integral part of the stopcock 70 in that the device 200 is permanently coupled to the side leg through which medication is injected. In this embodiment, the stopcock and shell form a single part that is then used with the IV line. Any number of techniques can be used to form such structure including suitable bonding and molding operations. In this embodiment, as with the other embodiments, the shell still at least partially encapsulates the interface, such as a luer connector or septum, that receives fluid from the fluid delivery device (e.g., syringe).

Figure 16:
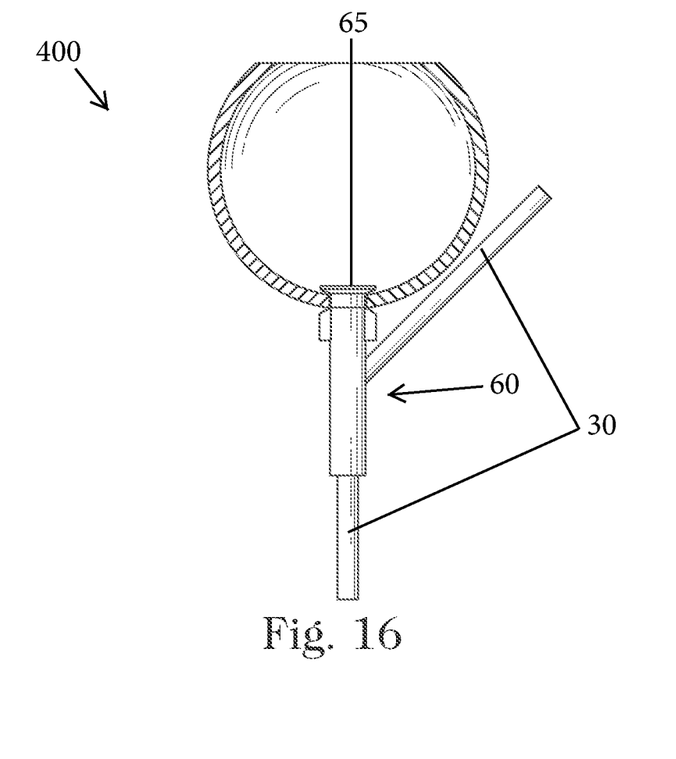
FIG. 16 is a cross-sectional view showing an injection port with integral protector.

FIG. 16 shows another embodiment in which a device 400 (which can have the same or similar construction as the device 200) is integral to the injection port 60 structure to form a single piece (part). The septum 65 is located within the hollow interior as in the embodiment of FIG. 7; however, since there are no slots, the IV tubing 30 passes and is routed outside the shell. The shell is thus coupled to the septum 65 and surrounds it.

Each of the first and second devices 100, 200 can be constructed so as to include a cap or cover structure that strategically covers either the main opening through which a syringe is inserted to access the needle penetrable membrane as in the case of device 100 and/or a cap or shield that covers the luer connector of the second device 200 and/or the main opening.

Figure 11:
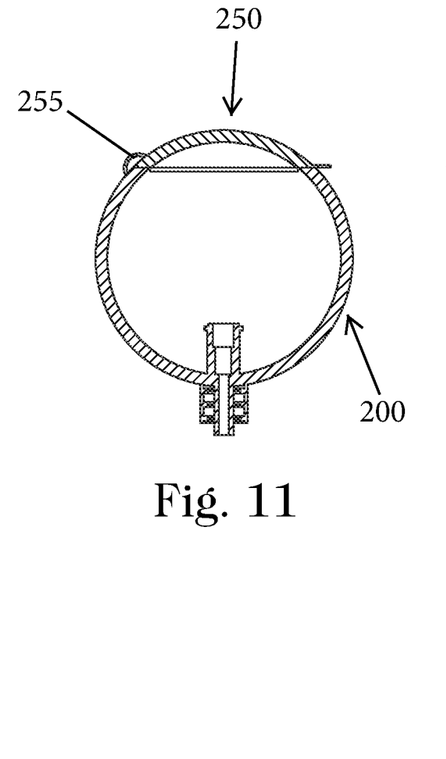
FIG. 11 is a longitudinal cross-sectional view of the device of FIG. 8 including a movable cover which is shown in a closed position.
Figure 12:
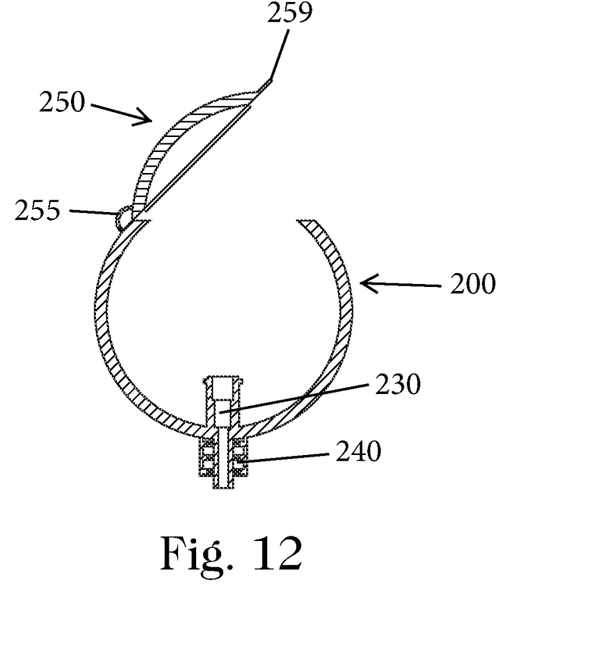
FIG. 12 is a longitudinal cross-sectional view of the device of FIG. 8 with the cover in an open position.

The device 100, 200 can be constructed such that it includes a cover or cap that can move between an open and closed position relative to the opening 105, 205. FIGS. 11 and 12 show a cover 250 that is part of the device 200; however, it will be readily understood that the cover 250 can be constructed in the same manner with respect to the device 100 and in such case, closes off the opening 105. The cover 250 can be constructed such that it is in the form of the truncated portion of the spherical shell (body) that was removed to form the opening 105, 205. The cover 250 thus completes the sphere and has a concave bottom surface and convex top surface as shown. It can be coupled to the remaining part of the device 100, 200 using any number of techniques, including the use of a hinge 255 as shown in the figures. To open the cover 250, a lip or tab 259 is formed at one edge of the cover 250. The cover can be spring loaded as well to ensure that it remain in a closed position.

In one embodiment, a cover or cap can be intended to cover at least the port septum 65 and in some embodiments, is intended to cover the opening 105. For example, a cap can be configured to fit over and be secured to the port septum 65 and since the cap is intended to be placed on the port septum 65 without having to touch the port septum 65, the cap can be disposed at a distal end of an elongated handle. A user thus holds the cap by the handle and inserts the cap through the opening 105 and by manipulating the handle, the cap is placed on the port septum 65. A friction fit or luer connection can be formed between the cap and the membrane.

Figure 13:
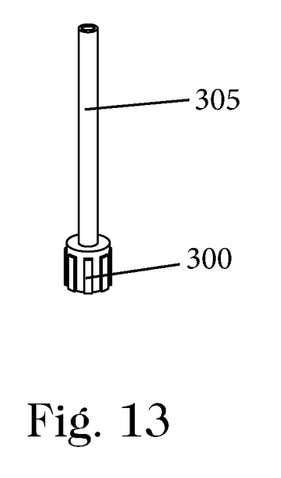
FIG. 13 is a side perspective view of a luer cap that is configured to cover the interface at which fluid is delivered to the IV system.

As with the first device 100, the second device 200 can include a cap or cover to shield the first connector part 230 from contaminants, such as airborne contaminants. As shown in FIG. 13, a luer cap 300 can be configured to mate with the first connector part 230 so as to cover and shield the first connector part 230. Since the user is not to insert a finger(s) through the opening 205, the luer cap 300 includes an elongated handle 305 that attaches as its distal end to the luer cap 300 and is of a length that permits the user to insert the luer cap 300 through the opening 205 and mate with the first connector part 230. For example, if the first connector part 230 has threads, the handle 305 can be rotated to cause rotation of the luer cap 300 to mate the luer cap 300 to the first connector part 230. It will be appreciated that the luer cap 300 can be a plastic cap and/or can contain an anti-microbial substance (e.g., Curos™ available from 3M).

Figure 14:
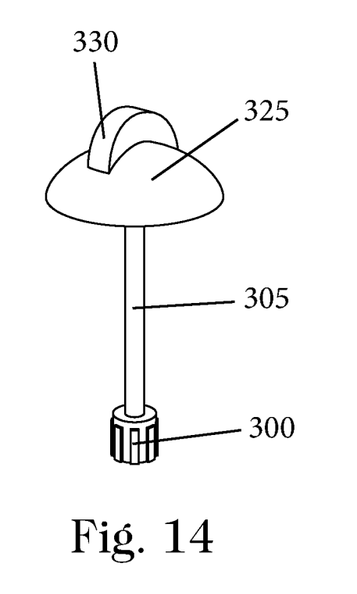
FIG. 14 is a side perspective view of a luer cap with a shield that is configured to cover the interface at which fluid is delivered to the IV system and the body of the device itself.

In yet another embodiment shown in FIG. 14, the proximal end of the handle 305 is connected to a cover 325 which is sized and shaped to fit and close the opening 205. For example, the cover 325 can have a disk (circular) shape. The cover 325 can have a handle 330 in the form of an upstanding protrusion that can be grasped by the user.

When the cover is designed to cover the opening 105, 205, a recessed landing can be formed about the opening for receiving the cover. The length of the handle is such that when the luer cap is coupled to the first connector part 230, the cover 325 covers the opening 205.

It will also be understood that the second device 200 can be used with other types of needleless injection ports that have a luer connector. For example, the system 10 can include a secondary branch defined by a segment of IV tubing. One end of the secondary branch terminates in a connector or the like (e.g., central catheter) in which the main IV line is also fluidly connected. The other end of the secondary branch terminates in a needless port which has an exposed luer connector that is configured to mate with the second device 200. For example, the exposed luer connector can be a female luer connector that mates with the male luer connector 240 of the second device 200. In this way, the second device 200 is fluidly connected to the exposed luer connector of the secondary branch.

In at least one embodiment of the present invention, the body of the device 100, 200 is formed so as to have an at least substantially spherically shape with the connector being contained in a bottom half of the body and the first opening is formed in a top 20% of the body which is truncated so as to define the first opening. For example, the body can be at least 70% spherical in one embodiment, at least 75% in another, at least 80% in another and at least 90% in yet another embodiment. However, it is possible to truncate the sphere at other locations that are at or above the equator of the sphere depending in part upon the overall size of the sphere, etc.

The injection interface to which the fluid delivery member mates for delivery fluid to the IV line is preferably located in a bottom one half of the body of the device (protector) and can be located in a bottom one third of the body of the device (protector) and further can be located in a bottom one fourth of the body of the device (protector). In general, the lower the injection interface is located in the hollow interior of the body (shell), the more difficult it is for contamination to occur since this injection interface is well shielded from surface contamination and the like. The above values are calculated based on the height of the body as measured from the open top edge of the shell to the bottom of the shell.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A device for shielding an injection port that is located along tubing that is part of an intravenous (IV) medication delivery system, the device comprising:
   a single piece spherical shaped body having a hollow interior, the spherical shaped body being truncated, at a location above a plane that passes through a center of the spherical shaped body and defines a diameter of the spherical shaped body, so as to define a first opening formed at a first end of the spherical shaped body for receiving a fluid delivery member into the hollow interior while the spherical shaped body at least partially encapsulates the injection port, the first opening having a diameter that is less than the diameter of the spherical shaped body and the first opening being configured for also receiving the injection port such that the spherical shaped body is configured to surround and extend above the injection port, the spherical shaped body being configured to retain and position the injection port below the first opening.

2. The device of claim 1, wherein the spherical shaped body is formed of a molded plastic material and wherein the spherical shaped body further includes a first slot that extends to the first end and opens into the first opening and terminates at an enlarged closed end that is enlarged relative to a main portion of the first slot that extends to the first end and the spherical shaped body also including a second slot spaced from the first slot, the second slot extending to the first end and opening into the first opening and terminating at a closed end, wherein the spherical shaped body includes first and second supports that are formed within the hollow interior and extend transversely thereacross and are formed such that at least a portion of the first slot including the enlarged closed end is located therebetween, wherein the first and second supports are configured and positioned for receiving and holding the injection port therebetween with at least a portion of the injection port passing through the enlarged closed end of the first slot, while the first and second slots are configured to allow passage of efferent and afferent limbs of the tubing while containing the injection port within the hollow interior.

3. The device of claim 2, wherein the first opening of the spherical shaped body is located at a top edge of the spherical shaped body and is opposite and coaxial with the enlarged closed end of the first slot.

4. The device of claim 3, wherein a side wall of the spherical shaped body is curved inwardly for positioning above the injection port and the first opening is positioned for placement directly above the injection port, wherein the first and second supports are configured for retaining the injection port in a coaxial arrangement relative to the first opening and the enlarged closed end of the first slot.

5. The device of claim 2, wherein at least a portion of the first slot is located opposite the second slot.

6. The device of claim 2, wherein a length of the first slot is greater than a length of the second slot.

7. The device of claim 2, wherein the enlarged closed end of the first slot is located at a second end of the spherical shaped body.

8. The device of claim 2, wherein a height of the spherical shaped body is selected such that a septum of the injection port is contained within at least a bottom one half of the hollow interior and the main portion of the first slot lies below top edges of the first and second supports.

9. The device of claim 2, wherein an intermediate region of each of the first support and the second support has an outwardly curved section such that the outwardly curved sections of the first support and the second support define a partial circular shaped space for receiving and supporting the injection port.

10. The device of claim 2, wherein a length of the first slot is located between the first and second supports and extend longitudinally along the first and second supports.

11. A device for shielding a stopcock that is located along tubing that is part of an intravenous (IV) medication delivery system, the device comprising:
   a body having a hollow interior and a first opening for receiving a fluid delivery member to allow passage of the fluid delivery member into the hollow interior, wherein the body has a spherical shape with a top portion being truncated so as to define the first opening, the spherical shaped body including an integral connector having a first connector part at a first end thereof and a second connector part at a second end thereof, the first connector part being disposed within the hollow interior and a second connector part being disposed external to the spherical shaped body, the first connector part being at least partially encapsulated within the spherical shaped body thereby preventing inadvertent contact with the first connector part, wherein the first connector part is configured to mate with fluid delivery member and the second connector part is configured to mate with a connector associated with the stopcock for establishing a fluid connection between the fluid delivery member and the tubing through the stopcock, wherein a top of the first connector part is located in a bottom half of the spherical shaped body in which a side wall of the spherical shaped body is curved outwardly, while the top portion of the spherical shaped body is curved inwardly for shielding the first connector part.

12. The device of claim 11, wherein the spherical shaped body and the connector are formed as a single molded plastic piece.

13. The device of claim 11, wherein the first connector part comprises a female luer connector and the second connector part comprises a male connector.

14. The device of claim 11, wherein the connector is coaxial with a center longitudinal axis that passes through a bottom hole of the spherical shaped body.

15. The device of claim 11, further including a cover that is coupled to the spherical shaped body and moves between an open position in which the first opening is accessible and a closed position in which the first opening is closed.

16. The device of claim 15, wherein the cover is pivotally coupled to the spherical shaped body by a hinge.

17. The device of claim 11, further including a luer cap disposed at a distal end of an elongated handle, the luer cap being configured to mate to the first connector part that comprises a female luer connector and the elongated handle having a length such that when the luer cap mates with the first connector part by a threaded coupling, a proximal end of the handle at least partially protrudes above the first opening so as to be accessible.

18. The device of claim 17, wherein the proximal end of the handle includes a shield that is configured to seal the first opening when the luer cap attaches to the female luer connector.

19. An intravenous (IV) medication delivery system comprising:
a source of fluid for delivery to a patient;
a main line that is in fluid communication with the source and terminates in a distal end that is configured for insertion into the patient;
an injection port that is in fluid communication with the main line and has an interface that is configured to allow a fluid from a fluid delivery device to be injected into the main line; and
a protective shell that at least partially encapsulates the interface of the injection port so as to prevent inadvertent contact with the interface, the protective shell including a first opening at a first end of the protective shell through which the fluid delivery device can pass to reach the interface of the injection port which is located within a hollow interior of the protective shell entirely below the first opening, wherein the protective shell has a truncated spherical shape with a through hole being formed in a second end of the protective shell and the injection port being disposed through the through hole in the second end of the protective shell and being axially aligned with the first opening.

20. The system of claim 19, wherein the interface is located in at least a bottom half of the hollow interior of the protective shell.

21. The system of claim 19, wherein the injection access port comprises an inline injection port.

22. The system of claim 19, wherein the fluid delivery device comprises a syringe.

23. The system of claim 19, wherein the first opening is configured to receive the fluid delivery device to allow passage of the fluid delivery device into the hollow interior while the protective shell at least partially encapsulates the injection port, the protective shell further including a first slot that opens into the first opening and terminates at an enlarged closed end that is enlarged relative to a main portion of the first slot that extends to the first opening, the protective shell having a second slot spaced from the first slot, the second slot opening into the first opening and terminating at a closed end, wherein the protective shell includes first and second supports that are formed within the hollow interior and extend transversely across the second end of the protective shell and are formed such that at least a portion of the first slot including the enlarged closed end is located therebetween, thereby defining an open space between the first and second supports and extending in a transverse direction, wherein the first and second supports are configured and positioned for receiving and holding the injection port therebetween, while the first and second slots are configured to allow passage of efferent and afferent limbs of tubing that is part of the main line, while containing the injection port within the hollow interior, wherein the enlarged closed end is configured for allowing insertion of both the injection port and one of the efferent and afferent limbs in a connected state.

24. The system of claim 23, wherein a side wall of the protective shell is curved inwardly above the injection port and the first opening is positioned directly above the injection port.

25. The system of claim 23, wherein a height of the protective shell is selected such that a septum of the injection port is contained within at least a bottom one half of the hollow interior.

26. A method for shielding a fluid access port that is located along tubing that is part of an intravenous (IV) medication delivery system and is configured to permit injection of a fluid into the tubing, the method comprising:
at least partially encapsulating the fluid access port within a hollow interior of a spherical shaped protective shell such that the fluid access port is surrounded by the spherical shaped protective shell and a top edge of the spherical shaped protective shell lies above a top edge of the fluid access port which lies within the protective shell with the top edge of the protective shell defining a first opening that has a diameter less than a diameter of the spherical shaped protective shell, the spherical shaped protective shell including a curved first slot that is open at the top edge and terminates in an enlarged closed end that is enlarged relative to a main portion of the first slot that extends to the top edge, and the step of partially encapsulating the fluid access port comprises inserting the fluid access port through the first opening and into the enlarged closed end to couple the fluid access port to the spherical shaped protective shell while the tubing that is fluidly attached to the fluid access port is simultaneously received within the first slot outside of the enlarged closed end.

27. A device for shielding an injection port that is located along tubing that is part of an intravenous (IV) medication delivery system, the device comprising:

a body having a hollow interior and a first opening at a top edge of the body for receiving a fluid delivery member to allow passage of the fluid delivery member into the hollow interior while the body at least partially encapsulates the injection port, the body further including a first slot that is open at a first end at the top edge of the body and has an opposite open second end that opens into a through hole formed through the body at a bottom end of the body, the through hole being configured to receive the injection port and having a greater width than the first slot, the body including a second slot spaced from the first slot, the second slot terminating at a closed end that is spaced from and not in direct communication with the through hole formed at the bottom end of the body, wherein the body includes first and second supports that are formed within the hollow interior and extend transversely across the body at the bottom end and are formed such that at least a lower portion of the first slot is located therebetween, the first and second supports defining a channel therebetween with the lower portion of the first slot extending along the channel, wherein the through hole opens into the channel, wherein the first and second supports are configured and positioned for receiving and holding the injection port therebetween, while the first and second slots are configured to allow passage of efferent and afferent limbs of the tubing while containing the injection port within the hollow interior.

\* \* \* \* \*